United States Patent
Ortiz et al.

(10) Patent No.: US 6,352,691 B1
(45) Date of Patent: Mar. 5, 2002

(54) THERAPEUTIC AFTER-SHAVE CARE LOTION

(76) Inventors: Robert Ortiz; Veronica Fernandez, both of 83-10 35th Ave. #1V, Jackson Heights, NY (US) 11372

( * ) Notice: Subject to any disclaimer, the term of this patent is extended or adjusted under 35 U.S.C. 154(b) by 0 days.

(21) Appl. No.: 09/569,250

(22) Filed: May 11, 2000

Related U.S. Application Data

(60) Provisional application No. 60/133,857, filed on May 12, 1999.

(51) Int. Cl.⁷ ............................. A61K 7/06; A61K 7/15
(52) U.S. Cl. ........................................ 424/73; 424/401
(58) Field of Search .................................. 424/73, 401

(56) References Cited

U.S. PATENT DOCUMENTS

| | | | |
|---|---|---|---|
| 4,228,163 A | 10/1980 | Bliss | 424/240 |
| 4,758,599 A | 7/1988 | Minetti | 514/844 |
| 4,784,849 A | 11/1988 | Tutsky | 424/73 |
| 4,944,939 A | 7/1990 | Moore | 424/73 |
| 5,034,221 A | 7/1991 | Rosen et al. | 424/73 |
| 5,047,166 A | 9/1991 | Weil | 252/132 |
| 5,541,220 A | 7/1996 | Ismail | 514/458 |
| 5,648,389 A | 7/1997 | Gans et al. | 514/557 |

FOREIGN PATENT DOCUMENTS

JP 06305932 * 11/1994

OTHER PUBLICATIONS

Aloe Vera as a Biologically Active Vehicle for Hydrocortisone Acetate, Davis et al.*
Japma, vol. 81, No. 1, Jan. 1991, pp. 1–9.*

* cited by examiner

*Primary Examiner*—James M. Spear
(74) *Attorney, Agent, or Firm*—Goldstein Law Offices, P.C

(57) ABSTRACT

A therapeutic after-shave care lotion composition for use in reducing inflammation and irritation of skin immediately following shaving, and for repairing skin damage resulting from shaving. The composition comprises Aloe Vera gel, Vitamin C (Ascorbic acid), Vitamin E (tocopherol), and Hydrocortisone Acetate.

4 Claims, No Drawings

THERAPEUTIC AFTER-SHAVE CARE LOTION

CROSS REFERENCES AND RELATED SUBJECT MATTER

This application relates to subject matter contained in provisional patent application Ser. No. 60/133,857, filed in the U.S. Patent Office on May 12, 1999.

BACKGROUND OF THE INVENTION

The invention relates to a therapeutic after-shave care lotion. More particularly, the invention relates to a skin care lotion for use after shaving for repairing skin damage from shaving and alleviating irritation and discomfort associated with shaving.

Modern society has dictated that hair removal in certain anatomical regions is a crucial part of grooming. Although waxing and electrolysis fulfill some hair removal needs, shaving is by far the most common hair removal operation—carried out by billions everyday, worldwide.

Shaving typically involves scraping the skin with a sharp blade. The aim is to shear the hairs until flush with the skin surface, without cutting into the skin surface. Razors have been developed which seek to follow the contours of the skin, so as to maintain the blade in a position where it cannot easily cut the skin. Because the skin surface is not always uniformly smooth, it is sometimes cut, and is typically abraded by the shaving operation.

Abraded skin becomes instantly irritated as a natural physiological response to help combat infection and promote healing so as to restore skin and its protection against infection. Accordingly, shaving often results in the immediate symptoms of pain, burning, itching, and dryness, especially among people with sensitive skin. The amount of discomfort and skin damage is in part related to the intensity of the inflammatory response.

One of the most common forms of skin irritation is known as pseudofolliculitis. Commonly known as "razor bumps", pseudofolliculitis often occurs immediately following the shaving operation. In men, pseudofolliculitis barbae commonly follows facial shaving. In women, however, it is more prevalent after either shaving, waxing or when using depilatory creams on legs, bikini lines, and underarm areas. In time, pseudofolliculitis can result in permanent "dark spotty scars" on the skin.

Pseudofolliculitis can also occur when pointed and sharp hairs re-emerge above the skin surface, but curl back toward the skin surface, penetrating and thus irritating the skin surface. This "ingrown hair" and the resulting irritation can greatly exacerbate the symptoms and discomfort following shaving.

Although pseudofolliculitis is such a common occurrence, to date few effective solutions and treatments have been proposed. The most obvious and effective treatment is to avoid shaving for several weeks. Foregoing such an important grooming task is not an option for many people. Other treatment attempts involve avoiding close shaving, using special razors or shavers, massaging the skin before and after shaving, and using warm water or lubricants to prepare and soften the skin and hair prior to shaving. These treatments are ineffective for most patients, in large part because the affected patient does not comply with treatment schedules which require extra effort but fail to show quick results.

Because these treatments are not always effective, treatment of pseudofolliculitis remains a major challenge among dermatologists and other skin care professionals.

While these treatments and techniques may be suitable for the particular purpose employed, or for general use, they would not be as suitable for the purposes of the present invention as disclosed hereafter.

SUMMARY OF THE INVENTION

It is an object of the invention to produce an after-shave skin care lotion which provides effective relief from discomforts associated with shaving.

It is another object of the invention that the after shave skin care lotion provides immediate relief of irritation symptoms upon application and initiates repair of damaged skin. Accordingly, the after-shave skin care lotion decreases the intensity of the natural inflammatory response caused by shaving and moisturizes and nourishes the damaged skin.

It is still another object of the invention to particularly combat pseudofolliculitis and provide instant relief thereof and prevent long term damage often associated therewith.

It is a further object of the invention that the after shave skin care lotion is well tolerated by both men and women and is suitable for use on most body parts where shaving is conducted.

It is a still further object of the invention to eliminate the necessity for tedious long term treatment to relieve shaving symptoms and discomforts.

The invention is a therapeutic after-shave care lotion composition for use in reducing inflammation and irritation of skin immediately following shaving, and for repairing skin damage resulting from shaving. The composition comprises Aloe Vera gel, Vitamin C (Ascorbic acid), Vitamin E (tocopherol), and Hydrocortisone Acetate.

To the accomplishment of the above and related objects the invention may be embodied in the form described in the 5 following description. Attention is called to the fact, however, that the examples given are illustrative only. Variations are contemplated as being part of the invention, limited only by the scope of the claims.

DETAILED DESCRIPTION OF THE PREFERRED EMBODIMENTS

According to the present invention, relief of symptoms and discomforts associated with shaving is provided by a composition of matter which may be referred to as a therapeutic after-shave care lotion. The composition comprises several active ingredients, including Aloe, Vitamin C, Vitamin E, and Hydrocortisone Acetate. Each of these ingredients serves a different function relating to reducing inflammation and irritation, or nourishing and restoring the skin.

Aloe extract is employed for its known moisturizing and moisture balancing properties. In addition, the Aloe promptly begins the process of skin healing and regeneration. Aloe also has bactericidal properties which help protect the damaged skin from bacterial infection. The preferred form for the Aloe component in the composition is as Aloe Vera pure gel.

Vitamin C, chemically known as ascorbic acid, is well known for its importance in the synthesis of collagen. Because collagen is a key component in skin, it is vital for skin regeneration. Topical application of Vitamin C and the subsequent absorption thereof greatly facilitates the production of collagen and thus the regeneration of skin damaged by shaving. Vitamin C is a powerful antioxidant. The Vitamin C is preferably added to the composition in oil form. If 300 mg Vitamin C oil is employed, it is preferably added in the range of 1 to 3 milliliters.

Vitamin E, chemically known as Tocopherol is a powerful biological antioxidant, which protects cellular membranes from oxidative destruction by reducing free radical membrane damage. Since Vitamin E is an effective moisturizing agent and because it aids in cell division, it greatly assists the regenerative process. Vitamin E is further useful for the purposes of this composition, in that it helps prevent the natural physiological inflammatory response following shaving. Vitamin E is also preferably added to the composition in oil form.

Hydrocortisone Acetate is employed in the composition to act as the main anti-inflammatory agent for reducing the effects of pseudofolliculitis. Hydrocortisone Acetate is a corticosteroid which provides temporary relief of itching, minor irritations and rashes when applied topically. It is preferable that the Hydrocortisone acetate component be included in cream form, in a strength ranging from 0.5% to 1.0%.

Now that the major components of the composition have been outlined, preferred proportions are as follows: 30 grams of 0.5% to 1.0% Hydrocortisone Acetate cream; 90 milliliters of 100% Aloe Vera organic gel; 5 milliliters of 10,000 IU Vitamin E oil; and 2 milliliters of 300 mg Vitamin C Oil.

The therapeutic after-shave care lotion composition as previously described, should be applied once, immediately following shaving. Multiple applications within a single day is not recommended, nor should the composition be used for the treatment of acne and other severe skin conditions.

In conclusion, when applied after shaving, the composition as described is effective in reducing the inflammation and irritation commonly associated with pseudofolliculitis, and in initiating repair of skin damaged by shaving.

What is claimed is:

1. A therapeutic after-shave care lotion for use in reducing inflammation and irritation of skin following shaving, comprising:

hydrocortisone acetate, provided in cream form of 0.5 to 1.0% strength;

aloe vera gel;

tocopherol, provided as 10,000 IU oil; and ascorbic acid, provided as 300 mg oil.

2. The therapeutic after-shave lotion as recited in claim 1, wherein the mixture as recited is formed in the proportions of 30 grams hydrocortisone acetate cream, 90 milliliters aloe vera gel, 5 milliliters tocopherol oil, and 2 milliliters ascorbic acid oil.

3. A therapeutic after-shave care method, for reducing inflammation and irritation associated with pseudofolliculitis, using a composition having hydrocortisone acetate provided as 0.5 to 1.0% hydrocortisone acetate cream, aloe vera, tocopherol provided as 10,000 IU oil, and ascorbic acid provided as 300 mg oil, comprising the steps of:

(a) shaving an anatomical area; and (b) applying the mixture to the anatomical area immediately following step (a).

4. The therapeutic after-shave care method as recited in claim 3, wherein the composition is in the proportion of 30 grams of hydrocortisone acetate cream, 90 milliliters of aloe vera gel, 5 milliliters of 10,000 IU tocopherol oil, and 2 milliliters of 300 mg ascorbic acid oil.

* * * * *